United States Patent [19]

Yoshida et al.

[11] Patent Number: 4,486,330

[45] Date of Patent: Dec. 4, 1984

[54] CLEANING COMPOSITION FOR ARTIFICIAL DENTURES

[75] Inventors: Akiyoshi Yoshida, Nara; Shigeru Kametaka; Shin'ichi Hayashi, both of Osaka, all of Japan

[73] Assignee: Rohto Pharmaceutical Co., Ltd., Osaka, Japan

[21] Appl. No.: 461,356

[22] Filed: Jan. 27, 1983

[30] Foreign Application Priority Data

Feb. 3, 1982 [JP] Japan .................................. 57/16100

[51] Int. Cl.$^3$ .......................... A16K 7/30; C11D 7/42
[52] U.S. Cl. ................................. 252/174.12; 424/50; 424/94; 435/200; 435/264
[58] Field of Search .................. 252/DIG. 12, 174.12; 424/50, 94; 435/264, 200

[56] References Cited

U.S. PATENT DOCUMENTS 3,880,742  4/1975  James et al. .......................... 435/200
4,335,101  6/1982  Stoudt et al. .......................... 425/50

FOREIGN PATENT DOCUMENTS 592449  10/1977  Switzerland .
122396   2/1971  United Kingdom .

Primary Examiner—John E. Kittle
Assistant Examiner—Mukund J. Shah
Attorney, Agent, or Firm—Lawrence Rosen

[57] ABSTRACT

A cleaning composition for an artificial denture which comprises $\beta$-1,3-glucanase as an essential component together with one or more of suitable carriers.

2 Claims, 2 Drawing Figures

CLEANING COMPOSITION FOR ARTIFICIAL DENTURES

The invention relates to the use of β-1,3-glucanase as a cleaning agent for an artificial denture and a cleaning composition containing the enzyme as an essential component.

Since L. R. Cahn suggested, in 1936, correlation between a stomatitis due to denture application and *Candida albicans,* one of pathogenic microorganisms present in a month (Ann. Dent., 3, p33, 1936), a denture spotting or staining, which is referred to as "denture plaque", has been studied as a problem not only of an appearance of the denture but also of a stomatic sanitation. As a result of the extensive studies, it has been recently elucidated that microorganisms and substances produced by them constitute a major cause for the denture staining. Having used a scanning electronmicroscope, Akira Irahara studied the time-dependent plaque formation on the surface of contact of a denture base with a mucous membrane of a mouth and found that a major microorganism adhered to the contact surface of the denture base was *Candida Berkhout,* inter alia, *Candida albicans* (Hokkaido Shika Ishi Gakkai Shi, 3, p56, 1975).

Recently, stomatitis caused by the adherence of *Candida albicans* to an artificial denture has become a great problem all over the world, especially in the United Kingdom and Northern European countries (see E. Budtz-Jorgensen and H. Löe, Scand. J. Dent. Res., 80, p457, 1972; and I. Olsen, Acta Odont. Scand., 33, p41, 1975). Accordingly, many researchers have made their efforts to develop an efficient cleaning agent, or cleanser, for an artificial denture, which can, in particular, remove *Candida albicans* from the surface of the denture.

Cleansers for an artificial denture which have been hitherto employed, such as alkaline peroxides, alkaline hypochlorites, acids and germicides, have various drawbacks and are unsatisfactory. Alkaline peroxides which are most popular among others, such as Polident® (Block Drug Co. Inc., Jersey City, N.J., the United States), Efferdent® (Warner-Lambert Co., Morris Plains, N.J., the United States), Steradent® (Reckitt & Colman Ltd., the United Kingdom) and Kleenite® (Vick Chemical Co., Wilton, Conn., the United States), have only weak cleaning effect.

Although the alkaline hypochlorites, such as Mersene® (Colgate-Palmolive Ltd., Dist New York, N.Y., the United States), are generally superior to alkaline peroxides in their cleaning effect, they have serious drawbacks that they not only erode metals contained in an artificial denture but also bleach and deteriorate the resin constituting the denture. Acids usable as a cleaning agent for an artificial denture, such as hydrochloric acid and phosphoric acid, also erode metals and deteriorate resins as alkaline hypochlorites. Germicides may kill microorganisms adhered to an artificial denture, but have no ability to remove them from the denture.

It has now been found that β-1,3-glucanase can be efficiently used as a cleaning agent for an artificial denture because it has a strong removing action of *Candida albicans* from the surface of the denture to which they adhere.

Thus, the invention provides the use of β-1,3-glucanase as a cleaning agent for an artificial denture.

β-1,3-Glucanase, which is also referred to as β-1,3-glucan hydrolase, β-1,3(4)-glucan glucanohydrolase, or laminaranase, is a hydrolase derived from various microorganisms and commercially available, for instance, under the following trade names: Zymolyase® 5000 and Zymolyase® 60000, both derived from *Arthrobacter luteus* (Kirin Brewery Co., Ltd., Japan); YL-5® derived from *Achromobacter iunatus* (Amano Seiyaku Co., Ltd, Japan); Celefro® derived from *Bacillus subtilis* (Novo Industri A/S, Denmark); Finizym® derived from *Aspergillus nigar* (Novo Industri A/S, Denmark); Novozym® 234 derived from *Trichoderma harzianum* (Novo Industri A/S, Denmark); and Kitalase® derived from *Rhizoctonia solani* (Kumiai Chemical Industry Co., Ltd, Japan).

In addition to the above, β-1,3-glucanase referred to as EC 3.2.1.6. or EC 3.2.1.39 (see Enzyme Nomenclature, Elsevier Publishing Co., 1965; Science 150:719, 1965) can be employed in the present invention as well as the enzyme derived from *Physarum polycephalum* (see Japanese Patent Publication (Kokai) No. 2310/1979).

The above enzymes are listed only by way of illustration and not limitative.

As stated above, and as will be shown in detail below, β-1,3-glucanase can remove *Candida albicans* from the denture. The removal of microorganisms from the denture has not been previously attained by any of the aforementioned prior art cleansers.

In addition to the remarkable effect just mentioned above, β-1,3-glucanase has a fungicidal action and prevents the generation of stomatitis due to denture application.

Furthermore, β-1,3-glucanase has no adverse effect to an artificial denture. Thus, as will be readily recognized by those skilled in the art, β-1,3-glucanase is most suitable cleanser for an artificial denture.

The enzyme, β-1,3-glucanase, is preferably combined with one or more of appropriate carriers to form a solid preparation, such as tablet, pill, granule, fine particle, powder, hard capsule, etc. The enzyme can also be formed into other preparations such as soft capsule, micro capsule, coated granule, coated tablet, and even in liquid preparations which are ready for use, so far as the enzyme can be stabilized therein.

Thus, the invention also provides a cleaning composition for an artificial denture which comprises β-1,3-glucanase as an essential component together with one or more of suitable carriers.

The carriers suitable for making the above preparations, such as excipients and adjuvants, may be selected, according to the type of the specific preparation, from those conventional to the art. Although not limited thereto, preferred carriers are lactose, starch, corn starch, magnesium stearate, calcium secondary phosphate, sorbitol, mannitol, carboxymethyl cellulose, tartaric acid, citric acid, sodium carbonate, sodium perborate, sodium bisulfate, sodium hexametaphosphate, hydroxypropyl cellulose, shellac sucrose, methyl cellulose, ethyl cellulose, hydroxypropyl methyl cellulose, low-substituted hydroxypropyl cellulose (LHPC), diethyl phthalate, dibutyl phthalate, talc, calcium sulfate, precipitated calcium carbonate, gelatin, acacia, carboxymethyl cellulose, polyvinyl pyrrolidone, sodium alginate, sodium chloride, sodium bicarbonate, calcium stearate, etc.

These preparations, except for liquid preparations, are dissolved in an appropriate liquid medium such as water just prior to use.

In addition to the carriers listed above, a buffer agent may be added to the cleaning composition of the invention so that the composition, when dissolved in an appropriate medium such as water, can show a pH ranging from 5 to 8 which is optimum to β-1,3-glucanase.

If desired, one or more of other various agents such as preservatives, coloring agents and perfumes may be added to the composition.

It has been previously known that enzymes such as protease (e.g. papain and trypsin), cellulase, lipase and mutanase have, though it is very weak, ability to remove *Candida albicans* from resins to which they adhere. On the other hand, the inventors have found that chymotrypsin, Alcalase ® (Novo Industri A/S, Denmark) and Pronase ® (Kaken Seiyaku Co., Ltd., Japan) have also a weak removing action on *Candida albicans* similar to the enzymes just mentioned above.

Any one of these enzymes cannot solely be employed as a cleanser for an artificial denture because of its low potency. However, one or more of these enzymes can be incorporated into the cleaning composition of the invention for the purpose of enhancement of the cleaning effect of β-1,3-glucanase.

It is preferred that the amount of β-1,3-glucanase contained in the composition of the invention is so adjusted that the concentration of the enzyme may amount to 0.3 unit/ml or more when the composition is dissolved in a predetermined amount of water.

In the above description, one unit of the enzyme is defined as the amount of the enzyme per milliliter of water required for reducing the optical density (at 880 nm) of a mixture, which has been obtained by the reaction of β-1,3-glucanase with a beer yeast suspension at 25° C. for 2 hours, to a value 30% lower than the initial optical density of the mixture. For instance, 0.3 unit of Zymolyase ® 5000 corresponds to 0.06 mg/ml of the enzyme.

Experiment 1

Figure 1:
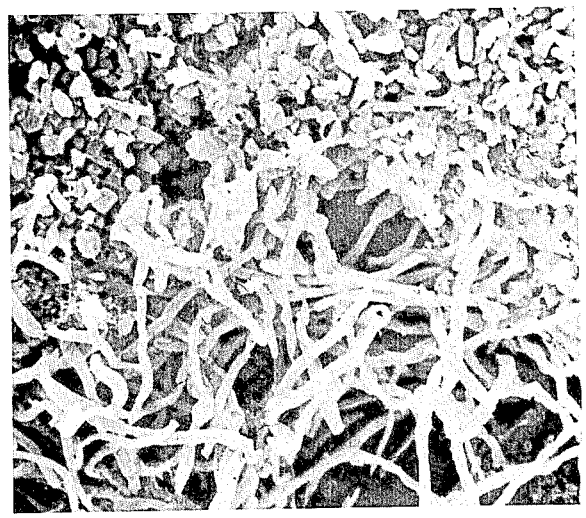
FIG. 1 is an electromicrophotographs of the surface of the artificial denture which has long been used; and, FIG. 2 is that of the denture treated with β-1,3-glucanase.

β-1,3-Glucanase enzymes of various origins and known cleaning agents for dentures are evaluated on their elimination effect on *Candida albicans*. For this purpose, synthetic resin plates (1 cm × 1 cm) were prepared by heat-polymerization of polymethyl methacrylate (Trade name: Acron, G-C Dental Industrial Corp., Japan). After rinsed with distilled water, the plates were placed in a Petri dish. Six ml of a *Candida albicans* suspension, which was available from the Department of Oral Bacteriology, Dental School, Hiroshima University, Japan, was poured onto the plates and incubated at 37° C. for one hour. The resultant plates to which the microorganisms had been adhered were rinsed with a physiological solution and placed in a fresh Petri dish.

Six milliliter of a test sample containing a predetermined amount of each of the cleansers listed in Table I was poured onto the plates, and the latter were kept at 37° C. for 5 minutes. After rinsed with distilled water, the plates were treated with 99% methyl alcohol for 10 minutes so as to fix the organisms possibly present thereon, subjected to the Gram staining and observed under a microscope to count the number of organisms remaining on the plates.

Control test was conducted in the same manner as described above using distilled water in place of the sample.

In each sample, the percentage of the number of the observed microorganisms relative to that of the control was calculated and shown in Table I. The smaller the percentage, the higher the potency of eliminating effect of microorganisms on the resin.

TABLE I

| Cleanser | Concentration % (w/v) | Number of Microorganisms (%) |
|---|---|---|
| Control | — | 100 |
| Polident ® | 1 | 50 |
| Duo ® | 1 | 30 |
| Papain | 0.005 | 130 |
| Chymotrypsin | 0.005 | 50–90 |
| Trypsin | 0.005 | 20 |
| Pronase ® | 0.005 | 50 |
| Alcalase ® 1.5 E | 0.005 | 30–50 |
| α-Amylase | 0.005 | 140 |
| Dextrase | 0.005 | 80 |
| Endo-N—acetylmulamydase | 0.005 | 70 |
| Pancreatin | 0.005 | 90 |
| β-1,3-glucanase available under the name of: | | |
| Zymolyase ® 60000 | 0.0005 | 0 |
| Zymolyase ® 60000 | 0.005 | 0 |
| Zymolyase ® 5000 | 0.006 | 0 |
| YL-5 ® | 0.005 | 10 |
| Celefro ® | 0.005 | 10 |
| Finizym ® | 0.005 | 10 |
| Novozym ® 234 | 0.005 | 30 |
| Kitalase ® | 0.005 | 10 |
| EC 3.2.1.6 | 0.005 | 0 |
| EC 3.2.1.39 | 0.005 | 0 |
| β-1,3-glucanase derived from *Physarum polycephalum* | 0.005 | 10 |
| Glanules in Example 16 | 1.5 | 0 |
| Fine particle in Example 9 | 1.5 | 0 |

Table I clearly shows that β-1,3-glucanase can completely eliminate *Candida albicans* from the resin even at a low concentration of 0.3 unit/ml. CL Experiment 2

Bacteriolysis action of β-1,3-glucanase was evaluated in a manner described below.

Zymolyase ® 60000 was added to 2 ml of a *Candida albicans* IFO 1385 suspension so as to make the final concentration of the enzyme to be 0.2 mg/ml, and the mixture was incubated at 37° C. Optical density at 660 nm ($OD_{660\ nm}$) of the mixture was measured at intervals of 10 minutes after addition of the enzyme, and the observed $OD_{660\ nm}$ values were compared with the initial value.

Table II shows the results of the measurements expressed by percentage of respective $OD_{660\ nm}$ values relative to the initial one. As will be easily understood, decrease of the percentage shows increase of bacteriolysis due to β-1,3-glucanase.

TABLE II

| Time (minutes) | $OD_{660nm}$ (%) |
|---|---|
| 0 | 100 |
| 10 | 19 |
| 20 | 5 |
| 30 | 5 |

TABLE II-continued

| Time (minutes) | OD$_{660nm}$ (%) |
|---|---|
| 40 | 5 |
| 50 | 5 |
| 60 | 5 |
| 70 | 5 |
| 80 | 5 |
| 90 | 5 |

Table II shows that *Candida albicans* is lyzed by β-1,3-glucanase in a short time.

Experiment 3

Elimination of microorganisms from an artificial denture by the action of β-1,3-glucanase was observed under an electronmicroscope.

Two piecies of plates (ca. 5–8 square mm) were cut from a coloured portion of the artificial denture which has long been practically used. The plates were thoroughly rinsed with a physiological solution. One of the plates was immersed and kept at 37° C. for one hour in 20 ml of a phosphate buffer (pH 7.0) containing 0.6 mg/ml of Zymolyase ® 5000. The other plate was treated as above except that the same buffer containing no enzyme was employed. Subsequently, both plates were rinsed with a physiological solution, subjected to the glutaraldehyde fixation, dehydrated and dried. Gold-paladium was then vacuum evaporated on the plates, and the latter was observed under a scanning electronmicroscopy.

Figure 2:
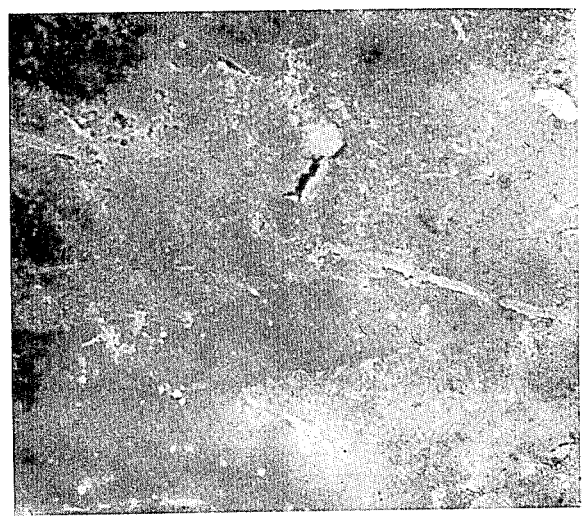

A lot of colonies of *Candida albicans* were found on the control plate, whereas no colony was found on the plate treated with Zymolyase ® 5000. FIGS. 1 and 2 show electromicrophotographs (1 × 1200) of the control plate and the plate treated with the enzyme respectively.

The following examples are presented by way of illustration of specific embodiments of the cleaning compositions for an artificial denture according to the invention.

Example 1 Powder

The following components are uniformly admixed, and each 0.1–1 g of the resultant mixture is folded in a suitable powder paper to make one usage unit.

| Component | Amount (part by weight) |
|---|---|
| Zymolyase ® 60000 | 1 |
| KH$_2$PO$_4$ | 41 |
| Na$_2$HPO$_4$.12H$_2$O | 161 |
| Lactose G | 97 |
| Total | 300 |

One usage unit of the powder is dissolved in 60–100 ml of water, and the solution is used as a cleaning solution for an artificial denture.

Example 2 Powder

The following components are uniformly admixed, and the mixture is folded in a suitable paper and used as described in Example 1.

| Component | Amount (part by weight) |
|---|---|
| Zymolyase ® 5000 | 10 |
| Alcalase ® 1.5E | 50 |
| KH$_2$PO$_4$ | 16 |
| Na$_2$HPO$_4$.12H$_2$O | 64 |
| Lactose G | 160 |
| Total | 300 |

Example 3 Powder

The following components are uniformly admixed, and the mixture is folded in a suitable paper and used as described in Example 1.

| Component | Amount (part by weight) |
|---|---|
| Kitalase ® | 10 |
| KH$_2$PO$_4$ | 70 |
| Na$_2$HPO$_4$.12H$_2$O | 10 |
| Lactose G | 210 |
| Total | 300 |

Example 4 Powder

The following components are uniformly admixed, and the mixture is folded in a suitable paper and used as described in Example 1.

| Component | Amount (part by weight) |
|---|---|
| Celefro ® | 40 |
| KH$_2$PO$_4$ | 16 |
| Na$_2$HPO$_4$.12H$_2$O | 64 |
| Lactose G | 180 |
| Total | 300 |

Example 5 Powder

The following components are uniformly admixed, and the mixture is folded in a suitable paper and used as described in Example 1.

| Component | Amount (part by weight) |
|---|---|
| β-1,3-glucanase derived from *Physarum polycephalum**  | 15 |
| KH$_2$PO$_4$ | 16 |
| Na$_2$HPO$_4$.12H$_2$O | 64 |
| Lactose G | 205 |
| Total | 300 |

Example 6 Powder

The following components are uniformly admixed, and the mixture is folded in a suitable paper and used as described in Example 1.

| Component | Amount (part by weight) |
|---|---|
| Finizym ® | 40 |
| Mutanase | 20 |
| KH$_2$PO$_4$ | 80 |
| Na$_2$HPO$_4$.12H$_2$O | 10 |
| Lactose G | 150 |

-continued

| Component | Amount (part by weight) |
|---|---|
| Total | 300 |

Example 7 Powder

The following components are uniformly admixed, and the mixture is folded in a suitable paper and used as described in Example 1.

| Component | Amount (part by weight) |
|---|---|
| Zymolyase ® 5000 | 1 |
| Kitalase ® | 9 |
| $KH_2PO_4$ | 16 |
| $Na_2HPO_4.12H_2O$ | 64 |
| Sodium lauroylsarcosinate | 10 |
| Sodium sulfite | 10 |
| Lactose G | 200 |
| Total | 300 |

Example 8 Granule and Fine Particle

| Component | Amount (part by weight) |
|---|---|
| Zymolyase ® 5000 | 10 |
| Trypsin | 30 |
| Lactose G | 150 |
| $KH_2PO_4$ | 16 |
| $Na_2HPO_4.12H_2O$ | 64 |
| Crystalline cellulose | 30 |
| Total | 300 |

The above components are uniformly admixed, and the mixture is compressed by a proper compressor, such as a roller compactor, to form a plate mass. The mass is broken by a crusher, granulated by means of an oscillating granulator and classified using an appropriate classifier, such as a gyroshifter.

Fine particle is obtainable by changing the conditions in the granulating process as stated above.

The resulting granule or fine particle (0.1–1.5 g) is dissolved in 60–100 ml of water and the solution is used as a cleaning solution for an artificial denture.

Example 9 Granule and Fine Particle

By the use of the following components, granule or fine particle is obtained in the same manner as described in Example 8. Two or three grams of the granule or particle is dissolved in 100–150 ml of water before use.

| Component | Amount (part by weight) |
|---|---|
| Zymolyase ® 5000 | 1 |
| Finizym ® | 9 |
| Chymotrypsin | 30 |
| $KH_2PO_4$ | 16 |
| $Na_2HPO_4.12H_2O$ | 64 |
| Sodium lauroylsarcosinate | 10 |
| Sodium sulfite | 10 |
| Crystalline cellulose | 20 |
| Lactose G | 140 |
| Total | 300 |

Example 10 Granule

| Component | Amount (part by weight) |
|---|---|
| Zymolyase ® 5000 | 10 |
| Chymotrypsin | 30 |
| Lactose G | 145 |
| $KH_2PO_4$ | 16 |
| $Na_2HPO_4.12H_2O$ | 64 |
| Crystalline cellulose | 20 |
| Sodium carboxymethyl cellulose | 15 |
| Total | 300 |

The above components are subjected to mixing and milling with addition of water, granulated by an appropriate granulator, dried and classified to give granules having a predetermined size range (Wet Granulating). The obtained granules can be used in a manner as described in Example 8.

Example 11 Tablet

| Component | Amount (part by weight) |
|---|---|
| Zymolyase ® 5000 | 5 |
| Alcalase ® | 10 |
| Lactose G | 39.5 |
| Microcrystalline cellulose | 5 |
| Magnesium stearate | 0.5 |
| $KH_2PO_4$ | 8 |
| $NaHPO_4.12H_2O$ | 32 |
| Total | 100 |

The above components are uniformly admixed, and the mixture is direct compressed to form tablets weighing about 100 to 300 mg. One or two tablets are dissolved in 60–100 ml of water, and the resulting solution is used as a cleaning agent for an artificial denture.

Example 12 Tablet

The following components are used to prepare tablets in the same manner as described in Example 11.

| Component | Amount (part by weight) |
|---|---|
| Kitalase ® | 10 |
| Chymotrypsin | 20 |
| Pronase ® | 10 |
| Lactose G | 39 |
| Talc | 0.5 |
| LHPC | 10 |
| Magnesium stearate | 0.5 |
| $KH_2PO_4$ | 52.5 |
| $Na_2HPO_4.12H_2O$ | 7.5 |
| Total | 150 |

Example 13 Tablet

Using the following components, tablets are prepared as described in Example 11.

| Component | Amount (part by weight) |
|---|---|
| Zymolyase ® 5000 | 20 |
| Endo-N—acetylmulamydase | 10 |
| Alcalase ® | 10 |
| Lactose G | 69.5 |
| Microcrystalline cellulose | 10 |
| Magnesium stearate | 0.5 |

| Component | Amount (part by weight) |
|---|---|
| KH$_2$PO$_4$ | 16 |
| Na$_2$HPO$_4$.12H$_2$O | 64 |
| Total | 200 |

Example 14 Effervescent Tablet

| Component | Amount (part by weight) |
|---|---|
| Zymolyase ® 5000 | 5 |
| Pronase ® | 20 |
| Anhydrous citric acid | 40 |
| NaHCO$_3$ | 100 |
| Polyoxyethylene nonylphenyl ether | 10 |
| Lactose G | 125 |
| Total | 300 |

The above components are uniformly admixed, and the mixture is compressed to make effervescent tablets, each weighing 2-3 g. The tablets must be stored under desication. One tablet is dissolved in 100-150 ml of water to give a cleaning solution for an artificial denture.

Example 15 Effervescent Tablet

Using the following components, effervescent tablets, each weighing 2-3 g, can be obtained according to the method described in Example 14.

| Component | Amount (part by weight) |
|---|---|
| Novozym ® 234 | 5 |
| Kitalase ® | 5 |
| Alcalase ® 1.5 E | 50 |
| Polyoxyethylene nonylphenyl ether | 10 |
| Sodium lauroylsarcosinate | 20 |
| Anhydrous citric acid | 40 |
| NaHCO$_3$ | 100 |
| Lactose G | 70 |
| Total | 300 |

Example 16 Effervescent Granules

| Component | Amount (part by weight) |
|---|---|
| Zymolyase ® 5000 | 1 |
| Kitalase ® | 9 |
| Alcalase ® 1.5 E | 50 |
| NaHCO$_3$ | 100 |
| Polyoxyethylene lauryl ether | 5 |
| Sodium lauroylsarcosinate | 5 |
| Methylparaben | 3 |
| Propylparaben | 2 |
| Sodium sulfite | 10 |
| Mannitol | 25 |
| Total | 210 |

The above components are uniformly admixed with addition of water, and the mixture is subjected to the wet granulating process described in Example 10. The wet granules thus obtained are dried and classified by a gyroshifter to give a granule A.

| Component | Amount (part by weight) |
|---|---|
| Anhydrous citric acid | 40 |
| Sodium ethylenediamine-tetraacetate | 10 |
| Mannitol | 37 |
| LHPC | 3 |
| Total | 90 |

The above components are treated in the same manner as described in granule A to give a granule B.

Twenty-one parts by weight of the granule A and 9 parts by weight of the granule B are thoroughly admixed in a V-type mixer. Each 2-3 g of the resulting mixture is folded in a suitable paper to make one usage unit. One unit of the mixture is dissolved in 60-100 ml of water.

Example 17 Effervescent Tablet

Twenty-one parts by weight of the granule A and 9 parts by weight of the granule B which are both described in Example 16 are thoroughly admixed in a V-type mixer, and the mixture is compressed to form effervescent tablets. One tablet containing 2-3 g of the mixture is used in the same manner as in Example 14.

What is claimed is:

1. A composition suitable for removing *Candida albicans* from artificial dentures which comprises a β-1,3-glucanase and a buffer; said β-1,3-glucanase and buffer being contained in the composition in such amounts that an aqueous solution thereof with a predetermined amount of water has a β-1,3-glucanase concentration of at least about 0.3 unit/ml and a pH of from about 5 to 8, wherein the β-1,3-glucanase is EC 3.2.1.6, EC 3.2.1.39, or derived from microorganisms selected from the group consisting of Arthrobacter luteus, Achromobacter iunatus, Bacillus subtilis, Aspergillus nigar, Rhizoctonia solani and Physarum polycephalum 2. A method of removing *Candida albicans* from artificial dentures which comprises immersing said dentures in an aqueous solution having a pH of from about 5 to 8 and β-1,3-glucanase in an amount effective to remove said *Candida albicans* therefrom, and which is at least 0.3 unit/ml.

* * * * *